United States Patent
Kimura et al.

(10) Patent No.: US 6,293,935 B1
(45) Date of Patent: Sep. 25, 2001

(54) ABSORBENT ARTICLE WITH LIQUID SHRINKABLE ELEMENTS

(75) Inventors: Mayumi Kimura; Hironori Kawasaki; Masahito Tanaka; Mitsugu Hamajima; Minoru Nakanishi; Takao Nakayama, all of Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/180,764
(22) PCT Filed: May 27, 1997
(86) PCT No.: PCT/JP97/01771
  § 371 Date: Jan. 13, 1999
  § 102(e) Date: Jan. 13, 1999
(87) PCT Pub. No.: WO97/45082
  PCT Pub. Date: Dec. 4, 1997

(30) Foreign Application Priority Data

May 28, 1996 (JP) .................................................. 8-133413
Jun. 4, 1996 (JP) .................................................. 8-141874

(51) Int. Cl.$^7$ ..................................................... A61F 13/15
(52) U.S. Cl. .................. 604/387; 604/378; 604/385.01; 604/385.03; 604/385.23
(58) Field of Search .................. 604/378, 387, 604/385.01, 385.03, 385.23

(56) References Cited

U.S. PATENT DOCUMENTS

| | | | |
|---|---|---|---|
| H1585 | * 8/1996 | Ahr | 604/378 |
| H1614 | * 11/1996 | Mayer et al. | 604/385.1 |
| H1634 | * 2/1997 | Oetjen et al. | 604/385.1 |
| 4,357,938 | * 11/1982 | Ito et al. | 128/287 |
| 4,425,130 | 1/1984 | DesMarais . | |
| 4,447,240 | * 5/1984 | Ito et al. | 604/385 |
| 4,475,913 | * 10/1984 | Hlaban | 604/387 |
| 4,576,596 | * 3/1986 | Jackson et al. | 604/370 |
| 4,578,066 | * 3/1986 | O'Connor | 604/366 |
| 4,623,342 | * 11/1986 | Ito et al. | 604/385 |
| 4,676,787 | * 6/1987 | Sergeant | 604/384 |
| 4,713,069 | * 12/1987 | Wang et al. | 604/378 |
| 4,731,071 | * 3/1988 | Pignuel | 604/385 |
| 4,808,177 | * 2/1989 | DesMarais et al. | 604/385.1 |
| 4,809,493 | * 3/1989 | Genba et al. | 57/238 |
| 4,834,733 | * 5/1989 | Huntoon et al. | 604/361 |
| 5,188,624 | * 2/1993 | Young, Sr. et al. | 604/378 |
| 5,324,278 | * 6/1994 | Visscheer et al. | 604/385.1 |
| 5,454,802 | * 10/1995 | Lindquist et al. | 604/385.1 |
| 5,567,265 | * 10/1996 | Zajaczkowski | 156/256 |
| 5,569,228 | * 10/1996 | Byrd et al. | 604/385.1 |
| 5,591,149 | * 1/1997 | Cree et al. | 604/378 |

(List continued on next page.)

FOREIGN PATENT DOCUMENTS

5836552   3/1983 (JP) .
59166146  9/1984 (JP) .
6156647   3/1986 (JP) .

Primary Examiner—John G. Weiss
Assistant Examiner—Michael Bogart
(74) Attorney, Agent, or Firm—Birch, Stewart, Kolasch & Birch, LLP (57) ABSTRACT

An absorbent article (1) comprising a liquid permeable top layer (10), a liquid impermeable back layer (20), and a liquid retentive absorbent member (30) interposed between the top layer (10) and the back layer (20), wherein the absorbent member (30) includes an absorbent sheet (31) having a thickness of 0.3 mm to 5 mm, the absorbent sheet being arranged such that a barrier cuff having a prescribed width is formed at the central portion of the top layer in the widthwise direction thereof, wherein said absorbent member is provided with liquid shrinkable members, which can elastically shrink upon the absorption of the liquid at the surface of said absorbent member facing said top layer and/or inside said absorbent member and in the vicinity of said surface, such that said absorbent member elastically shrinks over a prescribed length.

10 Claims, 9 Drawing Sheets

U.S. PATENT DOCUMENTS

| | | | | |
|---|---|---|---|---|
| 5,662,633 | * | 9/1997 | Doak et al. | 604/378 |
| 5,674,214 | * | 10/1997 | Visscher et al. | 604/385.1 |
| 5,688,259 | * | 11/1997 | Osborn, III et al. | 604/385.1 |
| 5,695,324 | * | 12/1997 | Weirich | 604/378 |
| 5,695,487 | * | 12/1997 | Cohen et al. | 604/384 |
| 5,702,380 | * | 12/1997 | Walker | 604/385.1 |
| 5,788,686 | * | 8/1998 | Ahr et al. | 604/389 |
| 5,827,258 | * | 10/1998 | McFall et al. | 604/385.1 |
| 5,853,401 | * | 12/1998 | Mayer et al. | 604/378 |
| 5,858,011 | * | 1/1999 | Brown et al. | 604/385.1 |
| 5,873,869 | * | 2/1999 | Hamons et al. | 604/385.1 |
| 5,885,264 | * | 3/1999 | Matsushita | 604/361 |
| 5,916,205 | * | 6/1999 | Olson et al. | 604/385.1 |
| 5,947,945 | * | 9/1999 | Cree et al. | 604/368 |
| 5,957,909 | * | 9/1999 | Hammons et al. | 604/387 |
| 5,961,508 | * | 10/1999 | Mayer et al. | 604/385.1 |
| 5,968,027 | * | 10/1999 | Cole et al. | 604/385.1 |
| 5,994,614 | * | 11/1999 | Wada et al. | 604/378 |

* cited by examiner

ABSORBENT ARTICLE WITH LIQUID SHRINKABLE ELEMENTS

This application is the national phase under 35 U.S.C. §371 of prior PCT International Application No. PCT/JP97/01771 which has an International filing date of May 27, 1997 which designated the United States of America, the entire contents of which are hereby incorporated by reference.

TECHNICAL FIELD

The present invention relates to an absorbent article, such as a sanitary napkin, an incontinent pad, a breastfeeding pad, and the like, including a liquid permeable top layer, a liquid impermeable back layer, and a liquid retentive absorbent member disposed between the top layer and the back layer. More particularly, the present invention is directed to an absorbent article which is satisfactory in body fluid absorptive ability and in fitness to the wearer, and which is capable of preventing liquid leakage irrespective of the quantity of body fluid and motion of the wearer.

BACKGROUND ART

In general, absorbent articles such as a sanitary napkin, an incontinent pad, a breastfeeding pad, and the like, are known to include a liquid permeable top layer, a liquid impermeable back layer, and a liquid retentive absorbent core disposed between the top layer and the back layer. Such an absorbent article is required to cause body fluid, such as blood, urine, and the like, to rapidly migrate to the absorbent core where it is absorbed and retained with no leakage.

As an absorbent article for absorbing/retaining body fluid without permitting leakage, there is known one as disclosed in Japanese Laid-Open Patent Publication No. 61 (1986)-56647; another as disclosed in Japanese Laid-Open Patent Publication No. 58 (1983)-36552; and still another as disclosed in Japanese Laid-Open Patent Publication No. 59 (1984)-166146.

In the absorbent article disclosed in Japanese Laid-Open Patent Publication No. 61 (1986)-56647, a top layer, a back layer, and an absorbent member are folded integrally, and overlaid at a widthwise central portion of the absorbent article.

In the absorbent article disclosed in Japanese Laid-Open Patent Publication No. 58 (1983)-36552, the absorbent member is an overlaid structure having two layers consisting of an upper layer and a lower layer, with a liquid impermeable barrier disposed therebetween.

In the absorbent article disclosed in Japanese Laid-Open Patent Publication No. 59 (1984)-166146, the absorbent member contains a fusible thermoplastic resin, this absorbent member being folded and overlaid at its widthwise central portion, and the absorbent member is partially, thermally bonded so that its folded form is retained.

Any one of these absorbent articles is designed such that, by forming the widthwise central portion thick in dimension, the widthwise central portion is reliably contacted with the body fluid leaking portion and a widthwise positional displacement is prevented, thereby avoiding a possible leakage of body fluid.

However, in the absorbent article disclosed in Japanese Laid-Open Patent Publication No. 61 (1986)-56647, since the back layer is disposed at the widthwise central portion between one absorbent member and another absorbent member and migration of the body fluid is interrupted by this back layer, a sufficient body fluid absorptive ability is not exhibited. Thus, there is the possibility that leakage of body fluid may occur.

Also, in the absorbent article as disclosed in Japanese Laid-Open Patent Publication No. 58 (1983)-36552, migration of the body fluid is interrupted by the liquid impermeable barrier at the widthwise central portion and a sufficient body fluid absorptive ability is not exhibited. Therefore, there is the possibility that leakage of body fluid may occur.

In the absorbent article disclosed in Japanese Laid Open Publication No. 59 (1984)-166146, since migration of the body fluid is interrupted by the melting thermoplastic resin contained in the absorbent member and a sufficient body fluid absorptive capacity is reduced, a sufficient body fluid absorptive ability is not exhibited. Thus, there is the possibility that leakage of body fluid may occur.

Further, as an absorbent article capable of absorbing/retaining a body fluid with no leakage, there has heretofore been known an absorbent article which employs a liquid-shrinkable member which tends to shrink elastically by absorbing a body fluid. Such an absorbent article has the advantage that it can easily be manufactured in the state that the liquid-shrinkable member has no elasticity.

An absorbent article employing a liquid-shrinkable material is that in which a plurality of liquid-shrinkable members are disposed in parallel relation to each other in the longitudinal direction of the absorbent article, generally over the entire central portion at the inside of the absorbent member in a thickness-wise direction. Thus, when a body fluid invades, the absorbent member is subjected to a shrinking treatment due to the shrinkage of the liquid-shrinkable members. Another absorbent article is that in which the liquid-shrinkable members are disposed outwardly of each side of the absorbent member in such a way as to cross the longitudinal direction of the absorbent article, so that when the body fluid invades, an external part of each opposing side of the absorbent member stands up due to the shrinkage of the liquid-shrinkable member. A third is that in which a liquid-shrinkable member is disposed on an external part of each opposing side of an absorbent member along the absorbent article, in a longitudinal direction thereof, so that when a body fluid invades, the absorbent article has a bent shape in the longitudinal direction due to the shrinkage of the liquid shrinkable member.

However, an absorbent article in which the absorbent member is subjected to a shrinking treatment has shortcomings in that since the liquid-shrinkable member is present generally over the entire central portion at the inside of the absorbing body in the thickness-wise direction thereof and since the absorbent article as a whole is provided with small irregularities, leakage tends to occur due to the motion of the wearer. With respect to the absorbent article in which the external part of each opposing side of the absorbent member stands up, they have shortcomings in that since the external part of each opposing side which stands up does not have a body fluid absorbing ability, leakage is likely to occur beyond the external part of each opposing side, due to the motion of the wearer. Also, with respect to the absorbent article which is bent in the longitudinal direction, since the liquid-shrinkable member is disposed at an external part of each opposing side of the absorbent body, the absorbent body does not shrink integrally with the liquid-shrinkable member, resulting in unfavorable possibilities wherein the absorbent article is not effectively bent, the fitness is degraded, and among all, the problem of liquid leakage, which is most likely to occur at the side edge of the absorbent article is not obviated. In addition, since no improvement is seen in absorptive capacity of a body fluid in any of the above conventional absorbent articles, they cannot appropriately cope with a large quantity of body fluid, thus inevitably resulting in leakage.

It is, therefore, the object of the present invention to provide an absorbent article which is excellent in body fluid absorptive capacity and fits nicely to the wearer's body, and which is capable of preventing the possible leakage of body fluid, irrespective of the quantity of body fluid and movement of the wearer.

DISCLOSURE OF THE INVENTION

As a result of an extensive search and development carried out by the inventors, it has been found that the above object can be achieved by arranging a specific absorbent sheet in a specific form in an absorbent member. The present invention is made based on this finding. According to the present invention, there is provided an absorbent article comprising a liquid permeable top layer, a liquid impermeable back layer, and a liquid retentive absorbent member interposed between said top layer and said back layer, wherein the absorbent member includes an absorbent sheet having a thickness of 0.3 mm to 5 mm, and the absorbent sheet is arranged to form an absorbent barrier cuff which is disposed at the central portion of the top layer in the widthwise direction thereof (this invention is hereinafter referred to as the "first aspect of the invention").

Also, the present invention has achieved the above object by providing an absorbent article comprising a liquid permeable top layer, a liquid impermeable back layer, and a liquid retentive absorbent member interposed between said top layer and said back layer, wherein the absorbent member is provided with liquid shrinkable members, which can elastically shrink upon the absorption of a liquid at the surface of the absorbent member facing the top layer and/or inside the absorbent member and in the vicinity of the surface, such that the absorbent member elastically shrinks over a prescribed length (this invention is hereinafter referred to as the "second aspect of the invention"). In addition, liquid shrinkable members referred to herein shrink upon absorption of a liquid such as water and a body fluid.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

Several embodiments of an absorbent article of the present invention (first aspect of the invention) will now be described specifically with reference to the drawings. In any one of the first three embodiments, a liquid permeable topsheet is used as a top layer and a liquid impermeable back sheet is used as a back layer.

Figure 1:
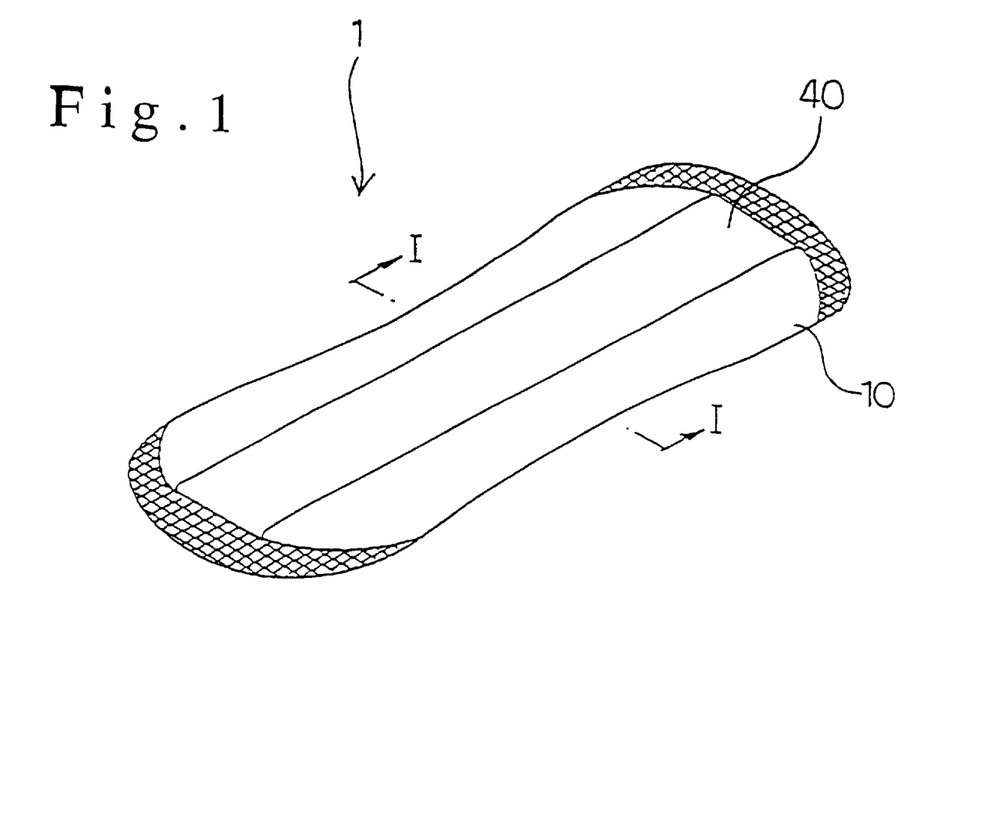
FIG. 1 is a perspective view showing an absorbent article according to a first embodiment of the present invention (first aspect of the invention)
Figure 2:
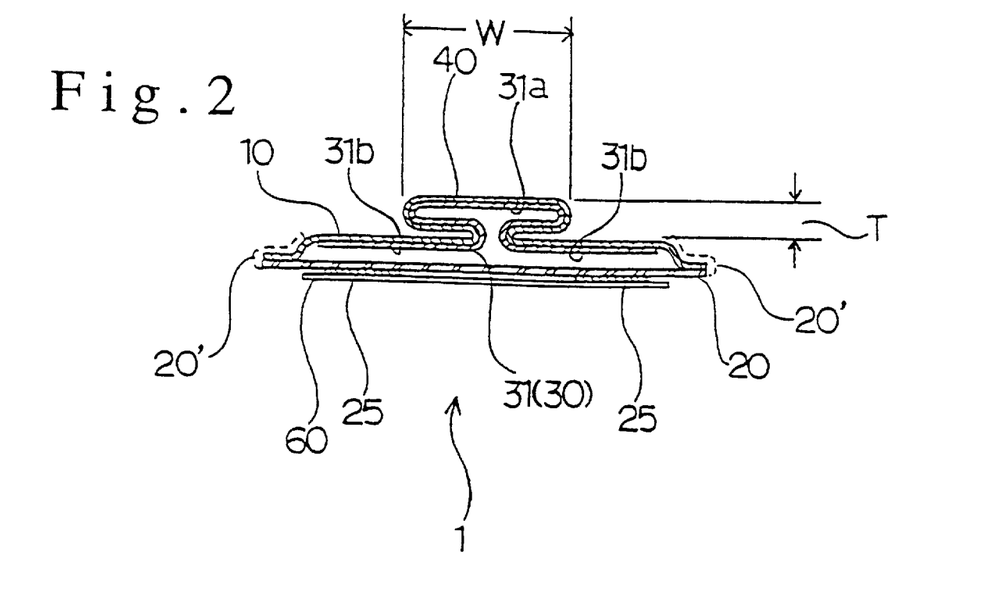
FIG. 2 is a sectional view, taken along line I—I of FIG. 1.

FIG. 1 is a perspective view showing the first embodiment of a sanitary napkin, as the first embodiment of the absorbent article of the present invention (first aspect of the invention), and FIG. 2 is a sectional view, taken along line I—I of FIG. 1.

The sanitary napkin 1 according to this embodiment includes a liquid permeable top layer 10, a liquid impermeable back layer 20, and a liquid retentive absorbent member 30 disposed between the top layer 10 and the back layer 20. This construction is the same as the prior art.

As shown in FIGS. 1 or 2, in the sanitary napkin 1 according to this embodiment, the absorbent member 30 includes an absorbent sheet 31 having a thickness of 0.3 mm to 5 mm, the absorbent sheet 31 being arranged such that an absorbent barrier cuff 40 having a prescribed width is formed on a widthwise central portion of the top layer 10. The thickness of the absorbent sheet 31 is necessarily 0.3 mm to 5 mm, preferably 0.3 mm to 3 mm, and more preferably 0.3 to 1.5 mm. If the thickness is less than 0.3 mm, it is difficult to provide a barrier cuff 40 capable of sufficiently exhibiting effects of the present invention that the fitness is improved, the absorptive capacity of body fluid is increased, and so forth. In addition, the sheet 31 tends to be twisted when folded, due to shortage of rigidity. In contrast, if the thickness is more than 5 mm, the rigidity of the absorbent sheet 31 is overly increased to spoil the fitness. Thus, the desired effect cannot be obtained and the perception of disorder is given to the wearer.

The absorbent member 30 consists only of the absorbent sheet 31. The absorbent sheet 31 includes a central band-like portion 31a, and a pair of side piece portions 31b, 31b connected to the opposing left and right side edges of the central band-like portions 31a. The side piece portions 31b, 31b are folded inwardly toward each other to the side of the back layer 20 at the left and right opposing side edges of the central band-like portion 31a and further folded outwardly away from each other. The portions of the absorbent sheet 31 thus folded are located along the longitudinal direction of the sanitary napkin 1 and the widthwise central portion of the absorbent sheet 31 is folded twice and overlays itself to form a band-like configuration. Free end portions of the two side piece portions 31b, 31b are extended proximately to the respective side edges of the back layer 20.

The entire surface of the absorbent sheet 31 is overlaid with the top layer 10, which is folded integrally with the absorbent sheet 31 such that it exhibits the same folded configuration as the absorbent sheet 31. Thus, the barrier cuff 40 is composed of the top layer 10 and the absorbent sheet 31. The overlaid structure of the absorbent sheet 31 and top layer 10 may be achieved by utilizing an adhesive agent or heat sealing, aside from the simple placement of the top layer 10 upon the absorbent sheet 31. The top layer 10 is extended to the perimeter of the absorbent sheet 31 and secured to the back layer 20 at the perimeter of the absorbent sheet 31.

The back layer 20 is applied at its outer surface with a viscous agent to thereby form two viscous portions 25, 25 in the longitudinal direction of the back layer 20. The viscous portions 25, 25 are each covered with a peelable paper 60. This peelable paper 60 is peeled off immediately before the sanitary napkin 1 is utilized, so that the viscous portions 25, 25 are exposed. The viscous portions 25, 25, when worn, adhere to the clothing in order to prevent slippage of the sanitary napkin 1.

The absorbent sheet 31 can be absorbent paper, nonwoven fabric, a pulp sheet made of fibers and a binder, fluff pulp, a sheet obtained by interposing a superabsorbent polymer between paper or nonwoven fabrics or between paper and nonwoven fabric in an overlaid configuration or a sheet made of a mixture of a superabsorbent polymer and fiber or hydrophilic fiber, and the like. A sheet having a mixture of a superabsorbent polymer and fiber or hydrophilic fiber is preferred for its absorptivity for body fluid (a sheet obtained by admixing a hydrophilic fiber, a superabsorbent polymer and a binder, and forming the admixture into a sheet like-shape). The superabsorbent polymer in the sheet may be dispersed either in layers or in three dimensions.

The above-described fiber or hydrophilic fiber preferably includes a cellulose fiber, such as wood pulp; a regenerated cellulose fiber, such as viscous rayon and cuprammonium rayon; a synthetic hydrophilic fiber, such as polyvinyl alcohol fiber and polyacrylonitrile fiber; and a synthetic fiber with the surface thereof rendered hydrophilic with a surface active agent, etc., such as polyethylene fiber, polypropylene fiber, polyethylene terephthalate fiber, polyethylene/polypropylene conjugate fiber, and polyethylene/polyethylene terephthalate conjugate fiber. Cellulose fibers are preferred for their satisfactory retention of hydrophilic properties.

The superabsorbent polymer which can be used in the absorbent sheet 31 is preferably one capable of absorbing and retaining 20 or more times as much liquid as its own weight and gelling upon liquid absorption. Such superabsorbent polymers include starch, crosslinked carboxymethylated cellulose, polyacrylic acid or a salt thereof, and a polyacrylate graft polymer. The polyacrylate is preferably sodium polyacrylate. Acrylic acid copolymers containing a comonomer, such as maleic acid, itaconic acid, acrylamide, 2-acrylamide-2-methylpropanesulfonic acid, 2-(meth)acryloylethanesulfonic acid, 2-hydroxyethyl (meth)acrylate or styrenesulfonic acid, in such a proportion that does not impair the performance as a superabsorbent polymer, can also be preferably used.

Particularly preferred are superabsorbent polymers capable of absorbing and retaining a large quantity of liquid through ionic osmosis and yet having no leaks even under pressure, comprising water-insoluble and hydrophilic crosslinked polymer particles which are obtained by polymerizing acrylic acid or an alkali acrylate (e.g., sodium or potassium), etc. followed by crosslinking for water insolubilization.

The binder which can be used in the formation of the absorbent sheet 31 preferably includes a thermally fusible bonding fiber and/or a strengthening assistant from the standpoint of wet strength of the resulting sheet.

The thermally fusible bonding fiber can be fibers which are fused upon heating and thus adhere to each other. Such thermally fusible bonding fiber includes polyolefin fiber, such as polyethylene, polypropylene, and polyvinyl alcohol; polyester fiber, polyethylene/polypropylene conjugate fiber, polyethylene/polyester conjugate fiber, low-melting polyester/polyester conjugate fiber, polyvinyl alcohol/polypropylene conjugate fiber having a hydrophilic surface, and polyvinyl alcohol/polyester conjugate fiber. The conjugate fibers may be either of a core sheath-type or a side-by-side type. These thermally fusible bonding fibers can be used either individually or as a mixture of two or more. The thermally fusible bonding fiber which can be preferably used in the present invention (the first aspect of the invention) includes polyvinyl alcohol fiber soluble in hot water and a core sheath-type polyester fiber. In general, these thermally fusible bonding fibers preferably have a fiber length of 2 to 60 mm and a fiber diameter of 0.1 to 3 deniers, particularly 0.5 to 3 deniers.

The strengthening assistant includes a polyamine epichlorohydrin resin, dialdehyde starch, sponge, and carboxymethyl cellulose.

A preferred absorbent sheet 31 comprises a hydrophilic fiber, a thermally fusible bonding fiber or a strengthening assistant, and a superabsorbent polymer, the superabsorbent polymer is not present on an absorbent surface of the absorbent sheet for absorbing liquid but distributed inside the absorbent sheet, and is adhered to the hydrophilic fiber constituting the absorbent sheet;

the superabsorbent polymer is spread at an amount of 5 to 300 g/m$^2$ of the absorbent sheet; and the absorbent sheet has a thickness of 0.3 to 1.5 mm.

A still preferred absorbing sheet 31 is composed of a fibrous structure made up of bulky hydrophilic fiber and thermally fusible bonding fiber or a strengthening assistant and superabsorbent polymer particles and having a thickness of 0.3 to 1.5 mm, in which the superabsorbent polymer particles do not exist on the absorbing surface of the absorbent sheet but are dispersed and fixed in the inside of the fibrous structure, and the superabsorbent polymer is used in a basis weight of 20 to 70 g/m$^2$.

In such a superabsorbent sheet, since a superabsorbent polymer is fixedly dispersed in a single sheet in a three dimensional pattern, the absorption ability of the superabsorbent polymer is effectively exhibited. Moreover, the gel blocking of the polymer is less. Accordingly, a body fluid tends to pass through the absorbent sheet smoothly. Thus, the absorbent sheet can advantageously be used in order to obtain a superabsorbent ability and an adequate liquid shrinkage in accordance with the quantity of body fluid.

In order for the barrier cuff 40 to be able to reliably contact the wearer without giving the perception of disorder to the wearer and in order for the absorbent sheet to exhibit a favorable absorptive capacity of body fluid at the barrier cuff 40, the barrier cuff 40 is preferably 10 mm to 50 mm in width W and 1 mm to 10' mm in height T, and more preferably 20 mm to 40 mm in width W and 1 mm to 5 mm in height T.

It is preferable that the folding width (widthwise distance from the left and right opposing side edges of the central band-like portion 31*a* to that point on the side of the back layer 20 of the central band-like portion 31*a* where the absorbent sheet 31 is folded back) of the absorbent sheet 31 is, in combination of those of the left and right opposing side portions, equal to or more than one half of the width of the central band-like portion 31*a*.

As the viscous agent for forming the viscous portions 25, 25 and as the peelable paper 60, any one selected from those which have heretofore been used can be used with no special limitation.

In the sanitary napkin 1 of this embodiment thus composed, when the barrier cuff 40 contacts the wearer, body fluid invades into the barrier cuff 40 and is absorbed primarily by the central band-like portion 31*a* of the absorbent sheet 31. Then, the part of the body fluid which is not absorbed at the central band-like portion 31*a* migrates, either directly or along the folded forms of the side piece portions 31*b*, 31*b*, to a layer on the side of the back layer 20, and is absorbed and retained in large quantities by the barrier cuff 40.

According to the sanitary napkin 1 of this embodiment, since the barrier cuff 40 having a prescribed width is formed on the widthwise central portion of the top layer 10, the barrier cuff 40 fits reliably to the body fluid leaking portion, so that a widthwise slippage of the sanitary napkin 1 is prevented.

In the sanitary napkin 1 of this embodiment, since the barrier cuff 40, which is formed on the widthwise central portion, is composed by laminating the absorbent sheets 31 in a band-like fashion, the absorptive capacity of body fluid which is absorbed at this portion, is large, and the body fluid is rapidly absorbed and retained within the barrier cuff 40 with no hindrance. Therefore, according to the sanitary napkin 1 of this embodiment, a sufficient body fluid absorptive ability is exhibited, and the migration of body fluid up to the left and right opposing side portions and the possible leakage of body fluid are effectively prevented.

According to the sanitary napkin 1 of this embodiment, since the side of the top layer 10 of the absorbent member 30 is the absorbent sheet 31 having a thickness of 0.3 mm to 5 mm on the side of the top layer 10 of the absorbent member 30, twisting rarely occurs, the perception of disorder is not produced in the wearer, and a sufficient body fluid absorptive capacity is exhibited.

According to the sanitary napkin 1 of this embodiment, the barrier cuff 40 is produced by folding the absorbent sheet 31 having a thickness of 0.3 mm to 5 mm and a width W of about 10 mm to 50 mm when combined with that of the top layer 10 and a height T of about 1 mm to 10 mm. Accordingly, it is reliably fitted to the wearer without giving the perception of disorder to the wearer, and exhibits a favorable body fluid absorptive capacity.

According to the sanitary napkin 1 of this embodiment, since the barrier cuff 40 is composed by folding a single absorbent sheet 31, the body fluid rapidly migrates through the barrier cuff 40 and is absorbed therein without being deposited along the absorbent sheet 31. Thus, the possible leakage of body fluid is effectively prevented.

According to the sanitary napkin 1 of this embodiment, since the top layer 10 is folded and is overlaid integrally with the absorbent sheet 31, a migration of the body fluid to the left and right opposing side portions along the top layer 10 is avoided. Thus, the possible leakage of body fluid is more efficiently prevented.

Figure 3:
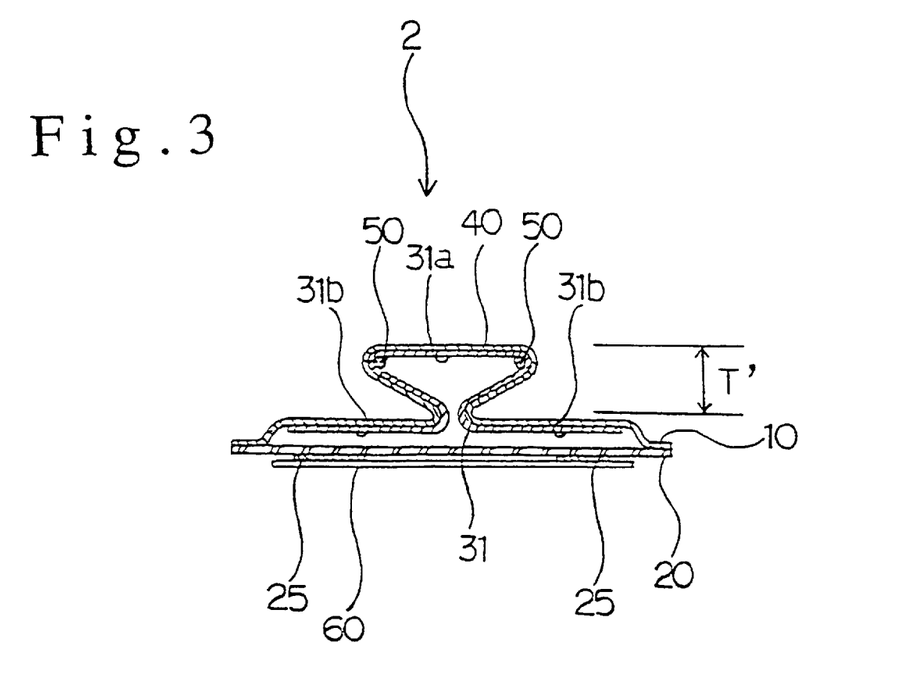
FIG. 3 is a vertical, sectional view corresponding to FIG. 2 of the first embodiment, showing an absorbent article according to a second embodiment of the present invention (first aspect of the invention)
Figure 4:
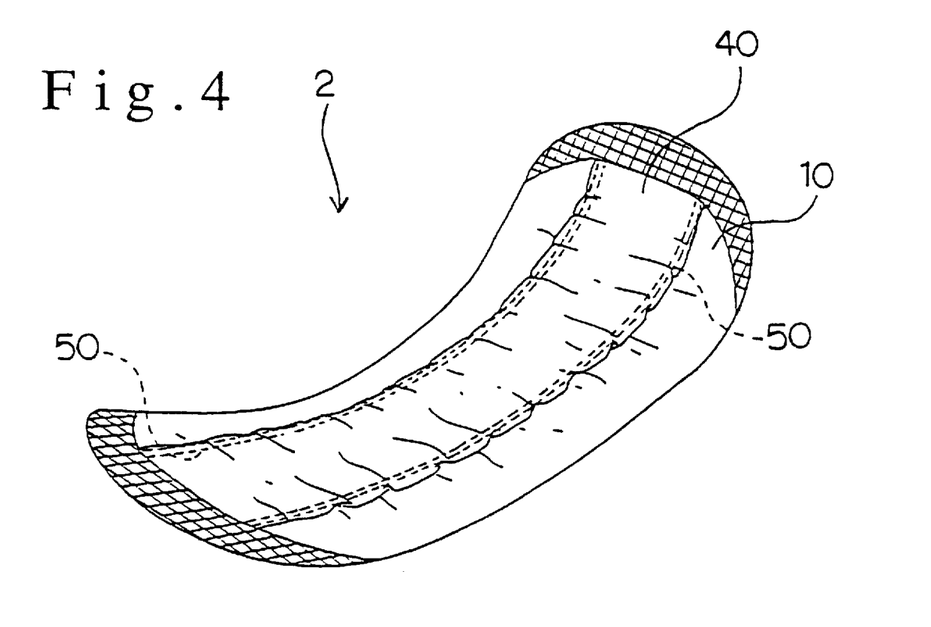
FIG. 4 is a perspective view showing the absorbent article of FIG. 3.

FIG. 3 is a vertical, sectional view corresponding to FIG. 2 in the first embodiment, showing the second embodiment of a sanitary napkin as an absorbent article of the present invention (first aspect of the invention), and FIG. 4 is a perspective view showing the sanitary napkin of FIG. 3. In this embodiment, those elements identical with that of the first embodiment of FIGS. 1 and 2 are denoted by identical reference numerals, and thus the description thereof is omitted.

As shown in FIG. 3, in a sanitary napkin 2 of this embodiment, the barrier cuff 40 is provided with a pair of elastic members 50, 50 inside each of the side edges of said barrier cuff 40 are located along the longitudinal direction of the barrier cuff 40 such that the barrier cuff shrinks along the longitudinal direction of the barrier cuff over a prescribed length.

In this embodiment, the elastic members 50, 50 are, in their expanded status, fixedly secured to a connection portion between a central band-like portion 31*a* and side piece portions 31*b*, 31*b* from the side of the back layer 20.

As the elastic members 50, 50, a film, a fiber, a foamed body and the like composed of a polymer of a number of rubbers, such as polyurethane, polybutadiene, isoprene and the like, ethylene-vinyl acetate, or a number of polyolefins having extensibility can be used. In order to exhibit a favorable effect without degrading the comfortable wearing perception, the elastic members 50, 50 are preferably 10 gf to 300 gf in stress at 30% expansion.

The elastic members 50, 50 are not particularly limited in position and length for arrangement. However, in order to bend the barrier cuff 40 such that they favorably comply with the wearer, the elastic members 50, 50 are preferably arranged over a length of 15% to 90% of the entire longitudinal length of the sanitary napkin 2. In accordance with the contraction of the elastic members 50,50 in the longitudinal direction, the barrier cuff 40 stands in the upward direction thereby more securely preventing liquid leakage. The height T' of the barrier cuff 40 becomes higher than that in the case where no elastic members are provided, and is preferably 1 to 30 mm, more preferably 3 to 30 mm.

All of the other construction other than the arrangement of the elastic members 50, 50 of this embodiment is the same as the aforementioned first embodiment. The absorbent sheet 31 is preferably composed of material other than fluff pulp. The reason is that an absorbent sheet using a fluff pulp occasionally ruptures with the shrinkage of the elastic members 50, 50.

According to the sanitary napkin 2 of this embodiment, the same function and effect as the first embodiment can also be obtained.

According to the sanitary napkin 2 of this embodiment, since the barrier cuff 40 is composed of an absorbent sheet 31 having a thickness of 0.3 mm to 5 mm, the elastic members 50, 50 can easily be secured to the barrier cuff 40.

According to the sanitary napkin 2 of this embodiment, the absorbent sheet 31 is shrunk by the elastic members 50, 50 over a prescribed length in the longitudinal direction and bent, as shown in FIG. 4, in the longitudinal direction in such a way to comply with the wearer's contacting part. The barrier cuff 40 is held in its upstanding posture on the wearer's skin side. Accordingly, a possible leakage of body fluid can more effectively be prevented.

According to the sanitary napkin 2 of this embodiment, since the elastic members 50, 50 are secured to the thin absorbent sheet 31, the frill-like irregularities formed at the barrier cuff 40 by shrinkage of the elastic members 50, 50 are comparatively small, the good touch to the wearer's skin is hardly degraded on the side of the top layer 10, and the comfortable wearing perception is maintained.

Figure 5:
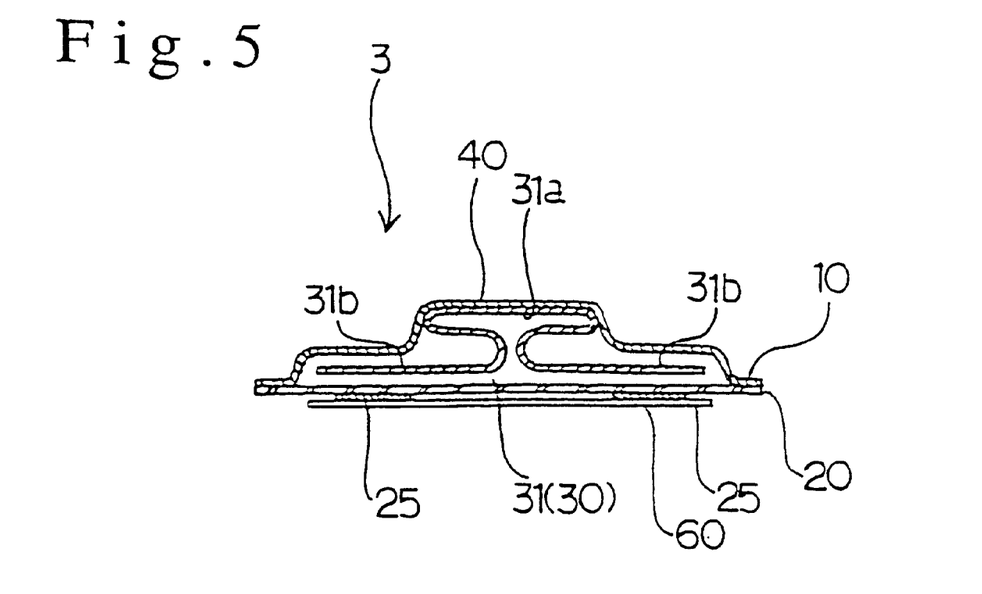
FIG. 5 is a vertical, sectional view corresponding to FIG. 2 of the first embodiment, showing an absorbent article according to a third embodiment of the present invention (first aspect of the invention)

FIG. 5 is a vertical, sectional view corresponding to FIG. 2 in the first embodiment, the third embodiment of a sanitary napkin as an absorbent article of the present invention (first aspect of the invention). In this embodiment, elements identical with the first embodiment of FIGS. 1 and 2 are denoted by identical reference numerals, with the description thereof being omitted.

As shown in FIG. 5, in the sanitary napkin 3 of this embodiment, the entire surface of the absorbent sheet 31 is not overlaid by the top layer 10, but rather only the unfolded exposed surface of the folded absorbent sheet 31 is overlaid by the top layer 10.

All of the other construction in this embodiment other than the arrangement of the top layer 10 is the same as the afore-mentioned first embodiment.

According to the sanitary napkin 3 of this embodiment, due to the provision that the barrier cuff 40 has a prescribed width and is formed on the widthwise central portion of the top layer 10, the barrier cuff 40 reliably contacts the body fluid leaking portion and the widthwise slippage of the sanitary napkin 3 is prevented.

In the sanitary napkin 3 of this embodiment, since the barrier cuff 40, which is formed on the widthwise central portion, is made by laminating the absorbent sheet 31 in the pattern of a band, the body fluid absorptive capacity is large in this location and therefore the body fluid can rapidly be absorbed/retained without interfering with the inside of the barrier cuff 40. Therefore, according to the sanitary napkin 3 of this embodiment, an effective body fluid absorptive ability can be exhibited, the body fluid will not migrate up to the left and right opposing side portions, and the possible leakage of body fluid is effectively prevented.

According to the sanitary napkin 3 of this embodiment, since the absorbent sheet 31 of the absorbent member 30 with a thickness of 0.3 mm to 5 mm is overlaid by the top layer 10, twisting seldom occurs, the perception of disorder is not conveyed to the wearer, and an effective absorptive capacity of body fluid can be exhibited.

According to the sanitary napkin 3 of this embodiment, the barrier cuff 40 is produced by folding the absorbent sheet 31 which has a thickness of 0.3 mm to 5 mm, a width W of about 10 mm to 50 mm when combined with that of the top layer 10 and a height T of about 1 mm to 10 mm. Accordingly, it is reliably fitted to the wearer without giving the perception of disorder to the wearer, and exhibits a favorable body fluid absorptive capacity.

According to the sanitary napkin 1 of this embodiment, since the barrier cuff 40 is made by folding a single absorbent sheet 31, the body fluid rapidly migrates through the barrier cuff 40 and is absorbed therein without being deposited along the absorbent sheet 31. Thus, the possible leakage of body fluid is more effectively prevented.

The present invention (first aspect of the invention) should not be limited to the above-mentioned first through third embodiments. The specific shape, dimension, etc. of each member can be appropriately modified without departing from the gist of the present invention. The folding form of the absorbent sheet, the covering form of the absorbent sheet of the top layer, the presence or absence of the elastic member, the presence or absence of the auxiliary sheet, and the like are mutually replaceable in the above respective embodiments.

Figure 6:
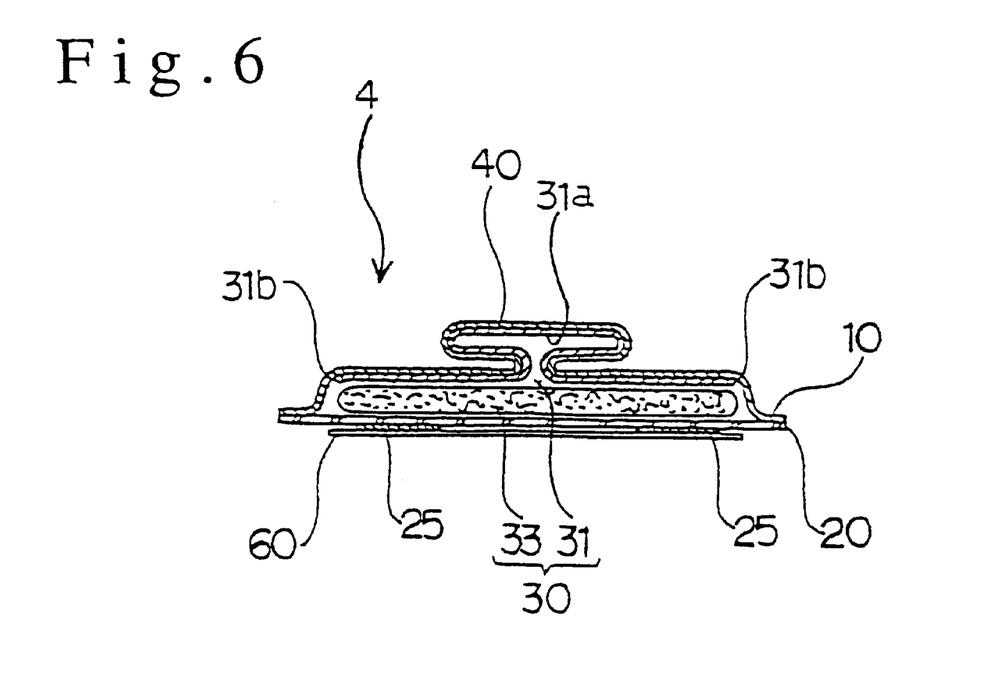
FIG. 6 is a vertical, sectional view corresponding to FIG. 2 of the first embodiment, showing an absorbent article according to another embodiment of the present invention (first aspect of the invention)

For example, in the first through third embodiments, an auxiliary sheet composed of a sheet similar to the absorbent sheet 31, and an absorbent pad such as pulp having a larger thickness than the auxiliary sheet may be arranged on the side of the back layer 20 of the absorbent sheet 31, so that the absorptive capacity at an area near the back layer 20 is increased. As such a sanitary napkin, FIG. 6 shows a sanitary napkin 4 in which an absorbent pad 33 is utilized with the absorbent sheet 31 as the absorbent member 30 of the first embodiment shown in FIGS. 1 and 2. The auxiliary sheet may be arranged only on the back layer 20 side of each of the left and right opposing side edges of the absorbent sheet 31 in the pattern of an elongated band, or it may be arranged over an area from one side edge of the absorbent sheet 31 to the other side edge in a widthwise enlarged pattern.

Figure 7:
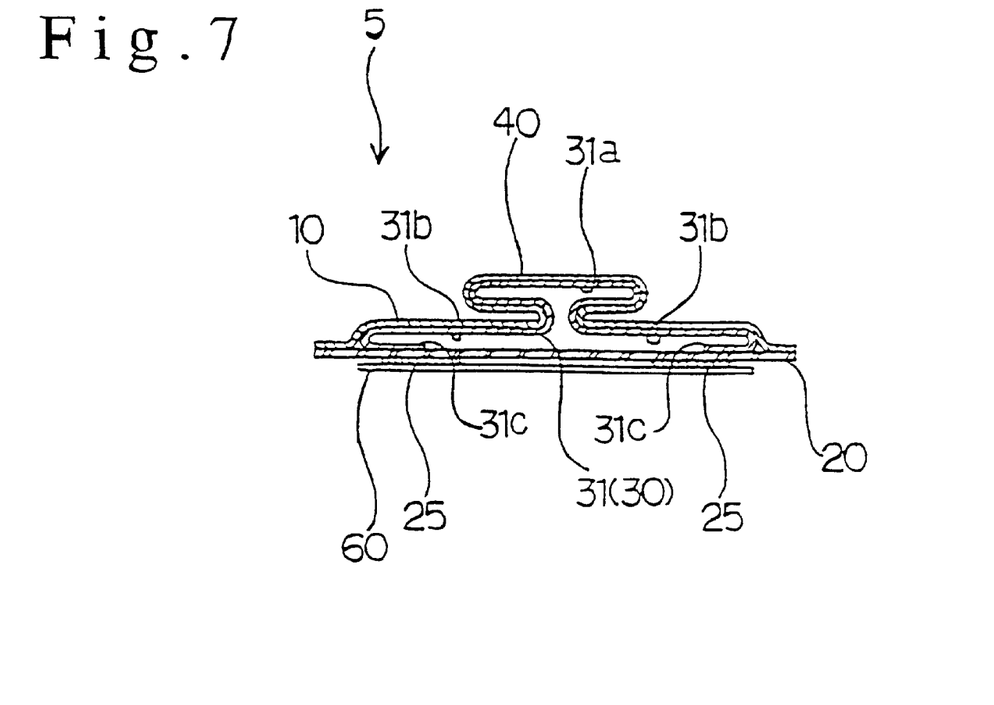
FIG. 7 is a vertical, sectional view corresponding to FIG. 2 of the first embodiment, showing an absorbent article according to still another embodiment of the present invention (first aspect of the invention)

Furthermore, in the first through third embodiments, the free end portions of the side piece portions 31b, 31b of the absorbent sheet 31 are not arranged in the vicinity of the side edges of the back layer 20. By forming an auxiliary layer obtained by folding the absorbent sheet 31 again in the neighborhood of the side edges of the back layer 20 and laminating them, the absorbent sheet 31 can provide the same effect as the above-mentioned auxiliary sheet. As such a sanitary napkin, FIG. 7 shows a sanitary napkin 5 in which, in the first embodiment of FIGS. 1 and 2, the absorbent sheet 31 is folded again in the neighborhood of the side edges of the back layer 20 to form the auxiliary portions 31c, 31c.

Figure 8:
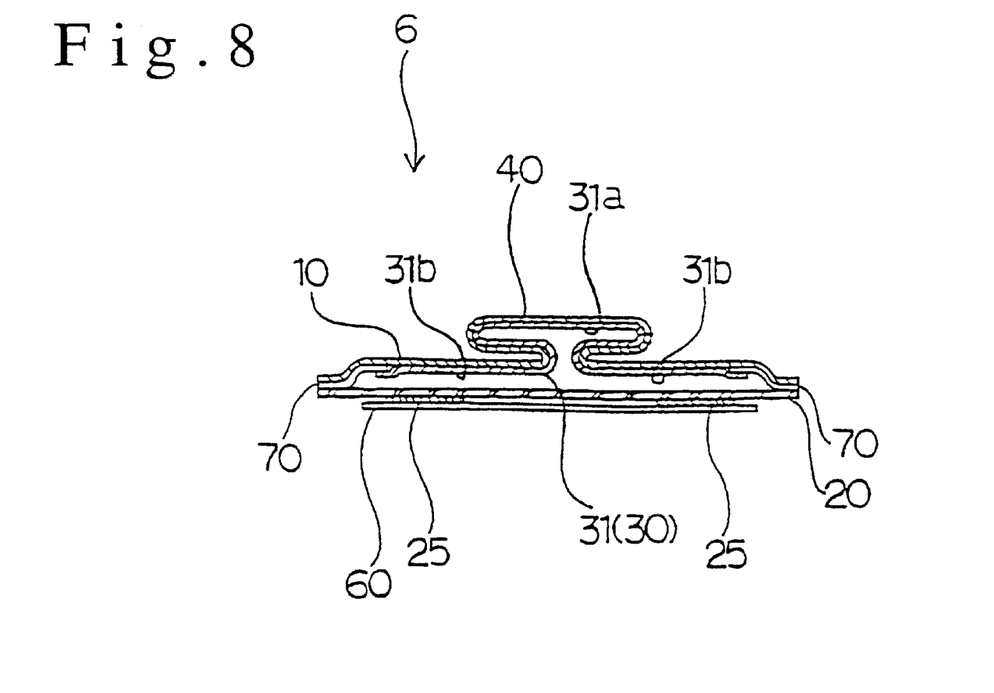
FIG. 8 is a vertical, sectional view corresponding to FIG. 2 of the first embodiment, showing an absorbent article according to still another embodiment of the present invention (first aspect of the invention)

In the first through third embodiments, it is also acceptable that the side edge portions of the back layer 20 are extended to form leakage preventive walls 20', 20' at the side outwardly of the absorbent member 30 as indicated by dotted lines of FIG. 2, or leakage preventive materials 70, 70 having liquid impermeable properties are arranged as shown in FIG. 8, so that the possible leakage of body fluid is more reliably prevented. In these cases, the leakage preventive walls 20', 20' or leakage preventive materials 70, 70 are slightly stood up by firmly thermally bonding the top layer 10 and the leakage preventive walls 20', 20' or leakage preventive materials 70, 70 to the back layer 20 at the perimeter of the absorbent sheet 31. Due to this arrangement, a more favorable effect can be obtained.

In the first through the third embodiments, the multilayered structure in the barrier cuff 40 may be formed by a plurality of absorbent sheets. In this case, the absorbent sheets may simply be arranged in superimposed relation, or may be joined under pressure at their entire opposing surfaces, or may be partially joined at their opposing surfaces by an adhesive agent, or the like.

In the first embodiment of FIGS. 1 and 2 and in the second embodiment of FIGS. 3 and 4, the absorbent sheet 31 and the top layer 10 may also be composed of a single sheet.

In the first and third embodiments, there may also be provided of the elastic members 50, 50 as in the second embodiment of FIGS. 3 and 4. In case there is an elastic member in the first and third embodiments and in the second embodiment, the liquid shrinkable member capable of being elastically shrunk by the absorbing body fluid can be employed as the elastic member 50,50.

In the first through third embodiment, the absorbent article may be a sanitary napkin, an incontinent pad, a breastfeeding pad, a surgical pad, or the like.

One embodiment of the absorbent article according to the present invention (second aspect of the invention) will now be described specifically with reference to the drawings. In this embodiment, a liquid permeable top sheet is used as a top layer, and a liquid impermeable back sheet is used as a back layer.

Figure 9:
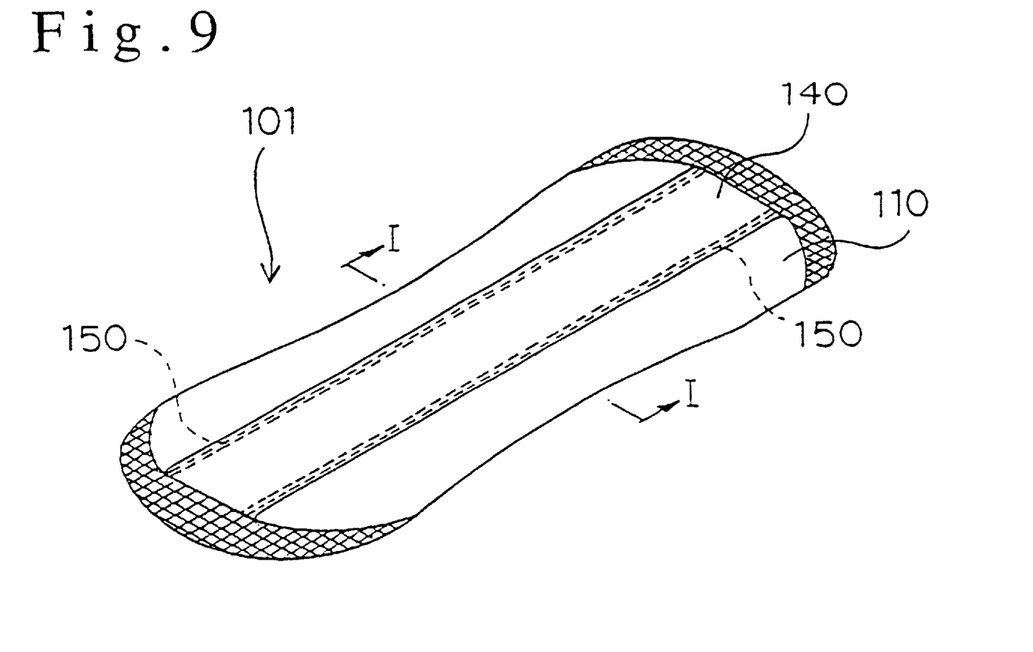
FIG. 9 is a perspective view showing an absorbent article as a further embodiment of the present invention (second aspect of the invention)
Figure 10:
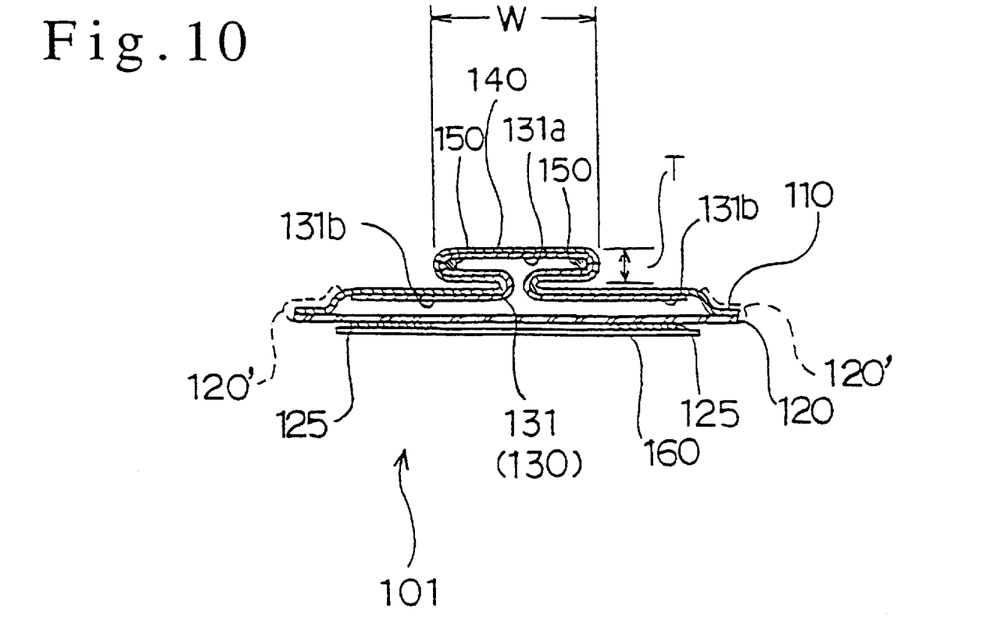
FIG. 10 is a sectional view taken along line I—I, of FIG. 9, when viewed in the direction as indicated by arrows.
Figure 11:
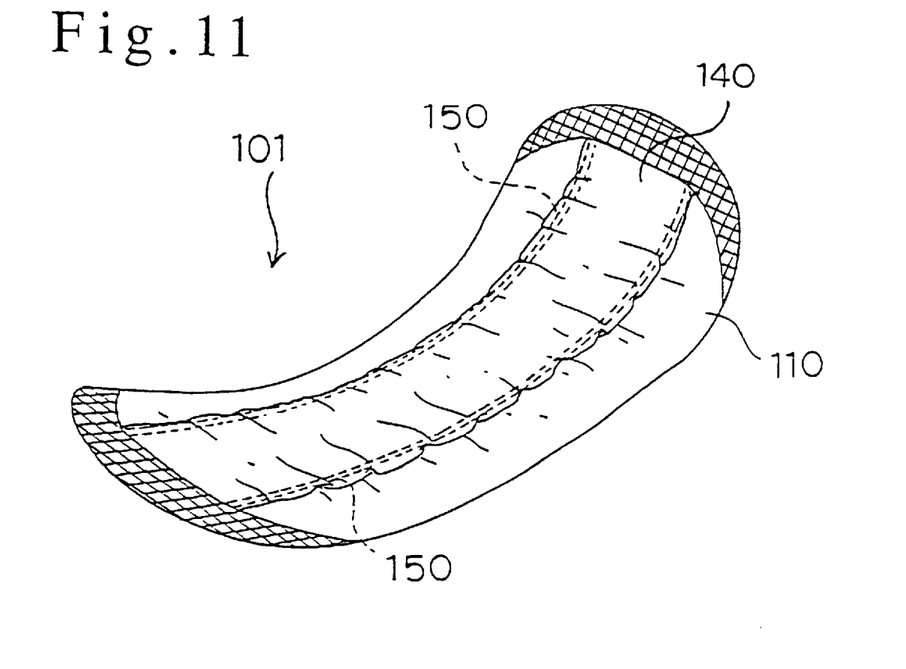
FIG. 11 is a perspective view showing a state of the absorbent article of FIG. 9 in which its liquid shrinkable member is in a condition after absorption of body fluid.
Figure 12:
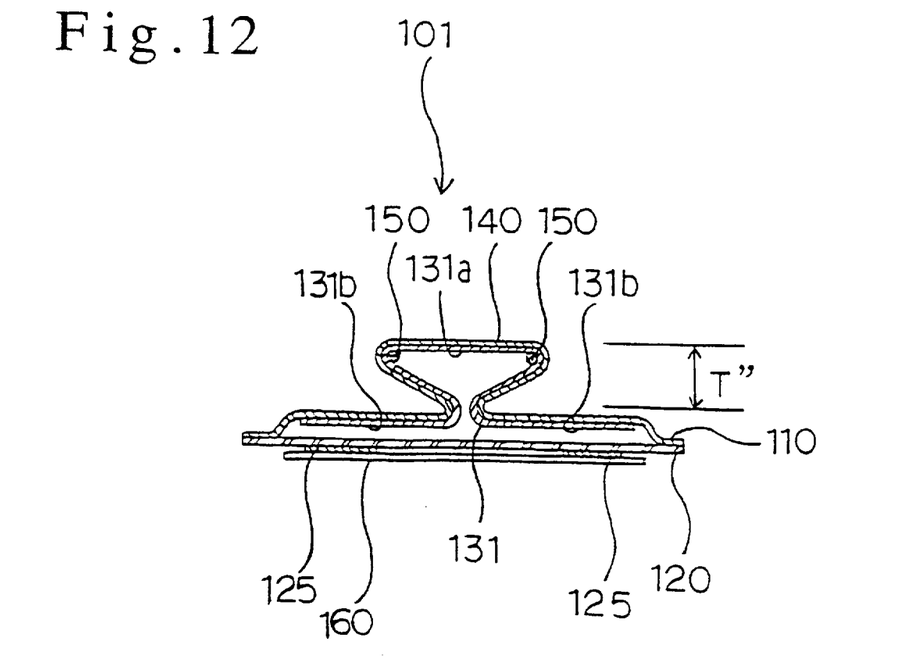
FIG. 12 is a vertical sectional view, taken along line I—I of FIG. 9, showing a state of the absorbent article of FIG. 9 in which its liquid shrinkable member is in a condition after absorption of body fluid.

FIG. 9 is a perspective view showing a sanitary napkin as one embodiment (hereinafter referred to as the fourth embodiment) of an absorbent article according to the present invention (second aspect of the invention), FIG. 10 is a sectional view of the sanitary napkin of FIG. 9 taken in line I—I and viewed in the direction as indicated by the arrows of FIG. 9, FIG. 11 is a perspective view showing the state of the sanitary napkin of FIG. 9 after absorption of body fluid, and FIG. 12 is a sectional view, taken on line I—I and viewed in the direction of the arrows of FIG. 9, showing the state of the sanitary napkin of FIG. 9 after the absorption of a body fluid.

As shown in FIGS. 9 or 10, a sanitary napkin 101 of this embodiment includes a liquid permeable top layer 110, a liquid impermeable back layer 120, and a liquid retentive absorbent member 130 interposed between the top layer 110 and the back layer 120.

In the sanitary napkin 101 of this fourth embodiment, the absorbent member 130 is provided with liquid shrinkable members 150, 150, which can elastically shrink upon absorption of liquid at the surface of the absorbent member 130 facing the top layer 110 and/or inside the absorbent member 130 and in the vicinity of the surface, such that the absorbent member 130 elastically shrinks over a prescribed length.

The fourth embodiment will now be described in detail. The absorbent member 130 consists only of an absorbent sheet 131 having a thickness of 0.3 mm to 5 mm. The absorbent sheet 131 is folded into an overlaying, serpentine configuration at the folding portions located along the longitudinal direction of the sanitary napkin 101, thereby providing the absorbent barrier cuff 140. The liquid shrinkable members 150, 150 are secured to the absorbent sheet 131. The absorbent sheet 131 is preferably 0.3 mm to 5 mm in thickness, more preferably 0.3 mm to 3 mm, and most preferably 0.3 mm to 1.5 mm. If the thickness is less than 0.3 mm, it is difficult to provide a barrier cuff 140 capable of sufficiently exhibiting the effects where the fitness is improved, the body fluid absorptive capacity is increased, and so forth. In addition, the sheet 131 tends to become twisted when folded, due to a shortage of rigidity. In contrast, if the thickness is more than 5 mm, the rigidity of the absorbent sheet 131 is excessively increased which spoils the fitness. Thus, the desired effect cannot be obtained and the perception of disorder is conveyed to the wearer.

The fourth embodiment is described in more detail. The absorbent sheet 131 is composed of a central band-like portion 131a and two side piece portions 131b, 131b connected to left and right opposing side edges of the central bandlike portion 131a. These two side piece portions 131b, 131b are folded inwardly toward each other to the side of the back layer 120 at the left and right opposing side edges of the central band-like portion 131a and then further folded outwardly away from each other. The folding portions of the absorbent sheet 131 folded in a manner as mentioned above are arranged in the longitudinal direction of the sanitary napkin 101 and the widthwise central portion of the absorbent sheet 131 is folded twice and overlaid to form a band-like configuration.

The free ends of the two side piece portions 131b, 131b of the absorbent sheet 131 are extended proximately to the side edges of the back layer 120, respectively.

The liquid shrinkable portions 150, 150 are secured to two connecting portions between the central bandlike portion 131a of the absorbent sheet 131 and the side piece portions 131b, 131b over the entire length thereof, from the inside of the connecting portions. Upon absorbing body fluid, the liquid shrinkable members 150, 150 cause the barrier cuff 140 to elastically shrink over the entire longitudinal direction to thereby form gathers.

The absorbent sheet 131 is overlaid over its entire surface by the top layer 110. The top layer 110 is folded in the same folding manner as the absorbent sheet 131 and is integral with the absorbent sheet 131. The overlaid structure formed by the absorbent sheet 131 and top layer 110 may be achieved by using an adhesive agent or a heat sealing material, aside from a simple placement of the top, layer 110 upon the absorbent sheet 131. The top layer 110 is extended to the perimeter of the absorbent sheet 131 and secured to the back layer 20 at a perimeter of the absorbent sheet 131.

With respect to the back layer 120, two viscous portions 125, 125 are formed on the outer surface thereof in its longitudinal direction by applying a viscous agent thereto. The viscous portions 125, 125 are covered with a peelable paper 160. The peelable paper 160 is peeled off immediately before the sanitary napkin 101 is worn, so that the viscous portions 125, 125 are exposed. The exposed viscous portions 125, 125 are attached to clothing, so that slippage of the sanitary napkin 101 can be prevented.

With respect to the absorbent sheet 131, one which is generally the same as the first embodiment of the first aspect of the invention can be used. The absorbent sheet 131 is preferably composed of other material than fluff pulp. The reason is that an absorbent sheet using fluff pulp occasionally ruptured caused by the shrinkage of the liquid shrinkable members 150, 150.

The absorbent sheet 131 is preferably one having a superabsorbent ability so that its liquid shrinkable member is not overly shrunk. Preferably, the absorbent sheet 131 is obtained by mixing a superabsorbent polymer to a fiber and forming the mixture into a sheet-like shape as in the first embodiment of the first aspect of the invention.

The binder, hot melting adhesive fiber, and strengthening assistant when the absorbent sheet 131 is formed by admixing the binder, are also the same as in the first embodiment of the first aspect of the invention.

As a preferable example of the absorbent sheet 131 and as a more preferable example of the absorbent sheet 131, there can be listed the same sheets as in the first embodiment of the first aspect of the invention. Such an absorbent sheet can preferably be used also with a view toward obtaining an appropriate degree of shrinkage of the liquid shrinkable member in accordance with the discharged quantity of body fluid.

A preferable width and thickness of the barrier cuff 140, and a folding width (a widthwise distance from the left and right opposing side edges of the opposing left and right side edges to the point where the absorbent sheet 131 is folded back at the back layer 120 side of the central bandlike portion 131a) of the absorbent sheet 131 is also the same as the first embodiment of the first aspect of the invention.

With respect to the viscous agent and the peelable paper 160 for forming the viscous portions 125, 125, that which has heretofore been used, can be used without any particular limitation as in the case of the first embodiment of the first aspect of the invention.

The liquid shrinkable members 150,150 can be selected from film, fiber, threads made of fiber, and foamed bodies, etc. with no particular restriction. Those capable of shrinking by 10% or more, particularly 20% or more, when impregnated with body fluid are preferred. Materials for the liquid shrinkable members 150,150 include modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and crosslinked fiber thereof; wool or silk modified in the same manner as described above; modified synthetic fiber, such as a partially saponified acrylonitrile series of fiber and vinilon fiber which is partially esterified by maleic acid; and yarns made of these fibers.

Combined twisted yarn made of a mixture of the above described shrinkable fibers and non shrinkable fibers or threads are also be used for preference in order to provide a liquid shrinkable member of improved strength when it is wet.

In order to bend the barrier cuff 140 into a configuration nicely complying to the wearer's contacting part, the liquid shrinkable members 150, 150 are preferably capable of shrinking at least in the generally central portions of the barrier cuff 140 in the longitudinal direction.

As the liquid shrinkable members 150,150 gets wet and elastically contracts in the longitudinal direction, the barrier cuff 140 extends in the upward direction, thereby more securely preventing liquid leakage. The height T" of the barrier cuff 140 becomes higher after the liquid shrinkable members 150,150 contract than before they contract, and is preferably 1 to 30 mm, more preferably 3 to 30 mm.

As the viscous agent for forming the viscous portions 125,125 and peelable paper 160, any product can be used without any particular limitation.

In the sanitary napkin 101 of the fourth embodiment, when the barrier cuff 140 contacts the wearer, the body fluid invades into the barrier cuff 140 and is absorbed primarily by the central bandlike portion 131a of the absorbent sheet 131. Any part of the body fluid which is not absorbed at the central band-like portion 131a, migrates either directly or along the folding forms of the side piece portions 131b, 131b, to a layer on the side of the back layer 120. At that time, the liquid shrinkable members 150, 150 are elastically shrunk due to the body fluid. As shown in FIGS. 11 or 12, the absorbent member 130 is bent in the longitudinal direction in such a way as to comply with the wearer's contacting part and the barrier cuff 140 extends in the upward direction.

In this way, according to the sanitary napkin 101 of the fourth embodiment, since the liquid shrinkable members 150, 150 are disposed at the inside of the absorbent member 130 and in the vicinity of the surface on the side of the top layer 110, the absorbent member 130 is effectively bent in the longitudinal direction in such a way as to comply with the wearer's contacting surface. Thus, irrespective of the movement of the wearer, the fitness is improved and leakage is effectively prevented.

According to the sanitary napkin 101 of this embodiment, the napkin 101 can easily be manufactured in a state where the liquid shrinkable members 150, 150 do not have elasticity and the absorbent member 130 is not shrunk.

According to the sanitary napkin 101 of the fourth embodiment, the barrier cuff 140 contacts the wearer and the body fluid invades into the barrier cuff 140 where it is absorbed/retained in large quantities primarily by the barrier cuff 140. Therefore, it is difficult for the body fluid to migrate up to the left and right opposing side portions. Thus, the possible leakage of body fluid is effectively prevented.

According to the sanitary napkin 101 of the fourth embodiment, the barrier cuff 140 is retained in its upstanding posture on the wearer's skin side due to shrinkage of the liquid shrinkable members 150, 150, and reliably contacts the wearer, whereby the fitness is improved. In addition, the barrier cuff 140 is located away from the lower layer and the body fluid is primarily absorbed by the central portion. Accordingly, even in case of a large quantity of body fluid or substantial movement of the wearer, the possible leakage of body fluid can be reliably prevented.

According to the sanitary napkin 101 of the fourth embodiment, since the barrier cuff 140 is composed of the absorbent sheet 131, the liquid shrinkable members 150, 150 can easily be arranged on the barrier cuff 140 by securing the liquid shrinkable members 150, 150 in the absorbent sheet 131 or disposing the liquid shrinkable members 150, 150 to the absorbent sheet 131 and securing it to the sanitary napkin 101 at the opposite end portions thereof When the liquid shrinkable members 150, 150 are secured to or disposed on the absorbent sheet 131, the gather-like irregularities formed on the absorbent member 130 by shrinkage of the liquid shrinkable members 150, 150 are comparatively small and therefore, the touch given to the wearer's skin is not degraded on the side of the top layer 110 so that a comfortable wearing perception can be maintained.

According to the sanitary napkin 101 of the fourth embodiment, since its multilayer structure at the barrier cuff 140 is achieved by folding a single absorbent sheet 131, the body fluid rapidly migrates through the barrier cuff 140 and is absorbed by the overall barrier cuff 140 without being deposited along the absorbent sheet 131. As a consequence, the possible leakage of body fluid can effectively be prevented.

According to the sanitary napkin 101 of the fourth embodiment, since the top layer 110 is folded/overlaid together with the absorbent sheet 131, it is difficult for the body fluid to migrate up to the left and right opposing side portions and also to migrate in the top layer 110. As a consequence, the possible leakage of body fluid can more effectively be prevented.

Figure 13:
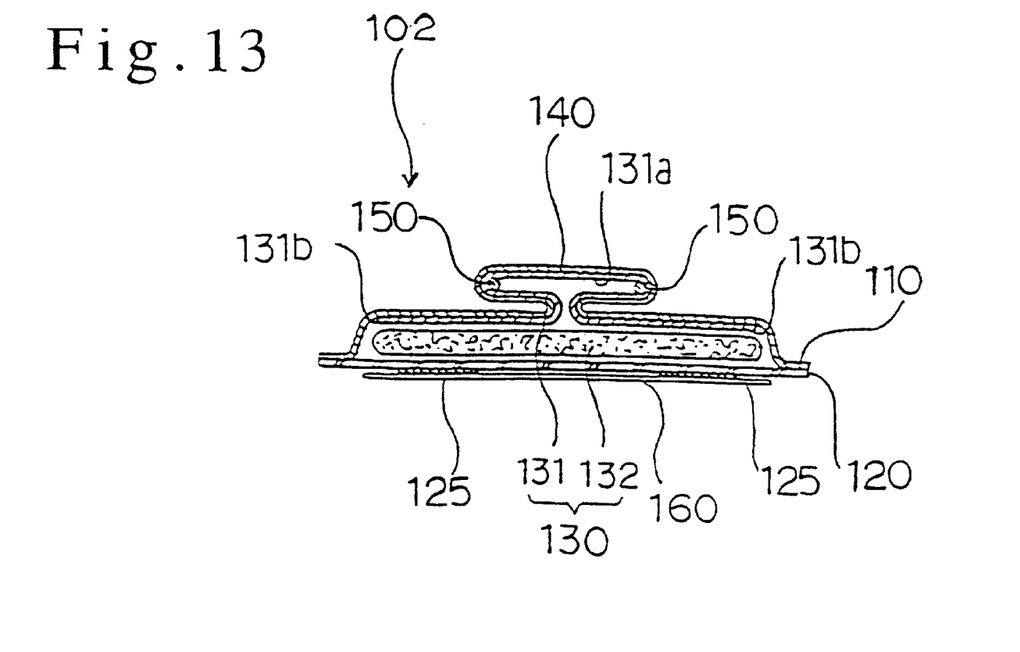
FIG. 13 is a vertical, sectional view corresponding to FIG. 10, showing an absorbent article according to another embodiment of the present invention (second aspect of the invention)

The present invention (second aspect of the invention) should not be limited to the fourth embodiment. The specific shape, dimension, etc. of each member can appropriately be modified without departing from the gist of the present invention For example, in the fourth embodiment, instead of the absorbent sheet 131, there may be provided only an absorbent pad, or as shown in FIG. 13, the absorbent member 130 may be the absorbent pad 133 in addition to the absorbent sheet 131.

Figure 14:
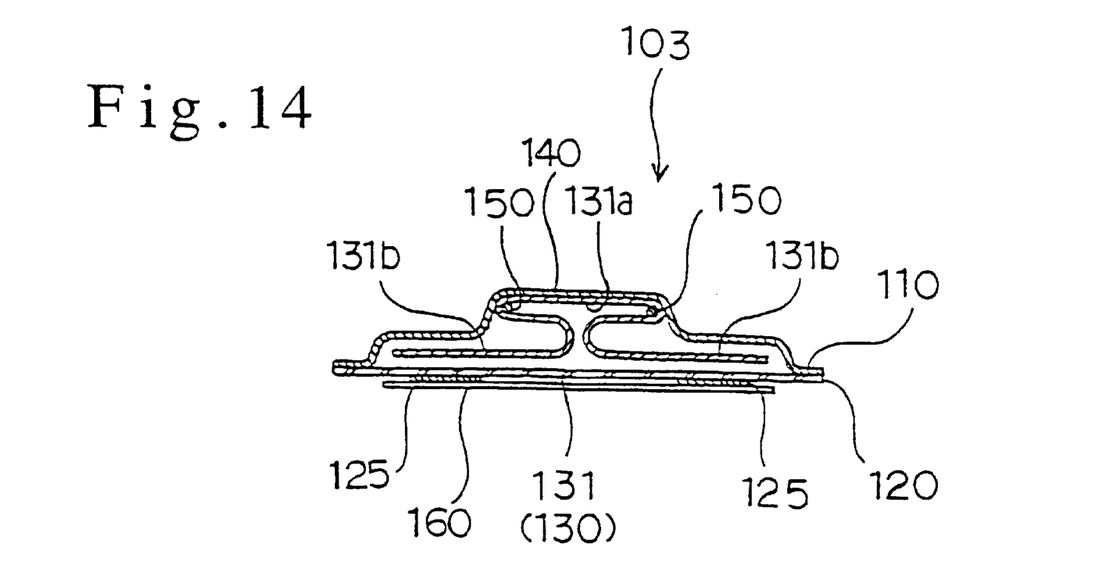
FIG. 14 is a vertical, sectional view corresponding to FIG. 10, showing an absorbent member according to still another embodiment of the present invention (second aspect of the invention)

Further, in the fourth embodiment, as shown in FIG. 14, it is also acceptable that the entire surface of the absorbent sheet 131 is not overlaid by the top layer 110, and thus only the unfolded exposed surface of the absorbent sheet 131 is overlaid by the top layer 110.

Figure 15:
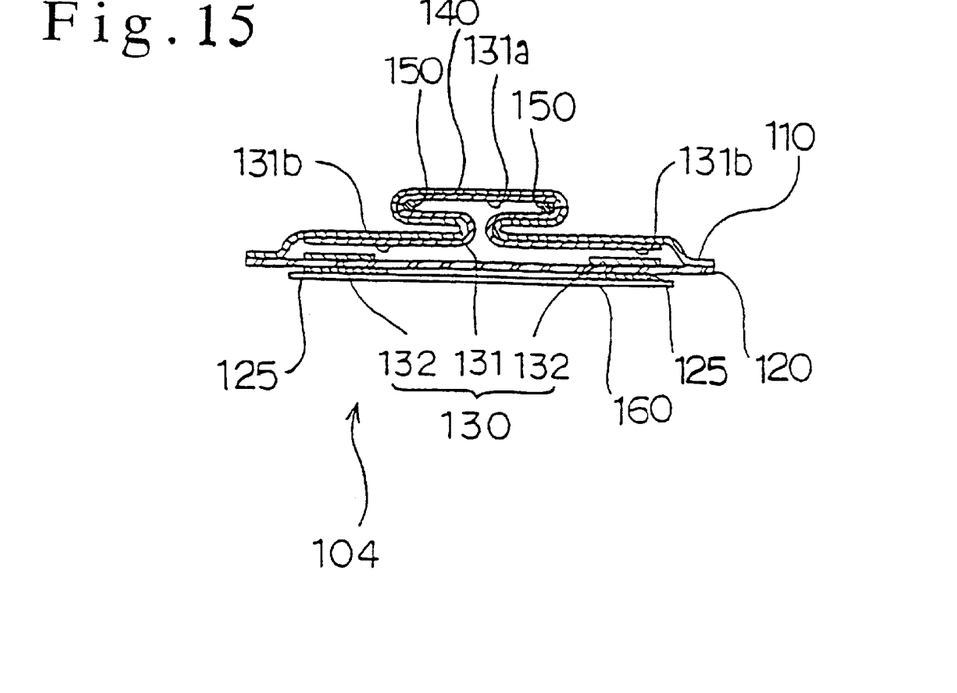
FIG. 15 is a vertical, sectional view corresponding to FIG. 10, showing an absorbent article according to still another embodiment of the present invention (second aspect of the invention)

In the fourth embodiment, as shown in FIG. 15, it is also acceptable that an auxiliary sheet 132 composed of a sheet similar to the absorbent sheet 131, is disposed between the absorbent sheet 131 and the back layer 120, to thereby compose the absorbent member 130, so that the body fluid absorptive capacity is increased in an area near the back layer 120.

Figure 16:
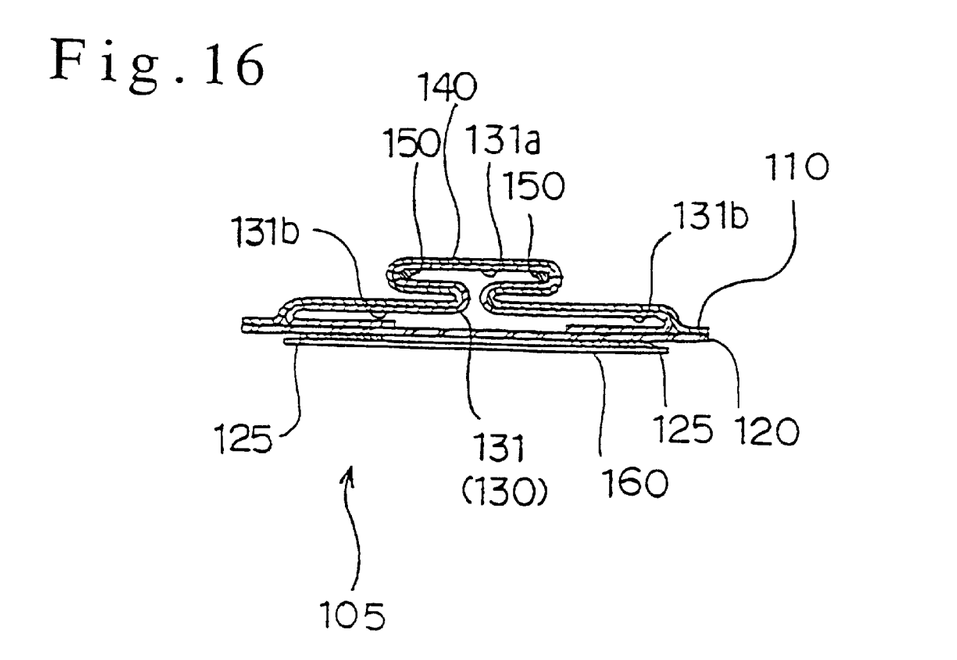
FIG. 16 is a vertical, sectional view corresponding to FIG. 10, showing an absorbent article according to still another embodiment of the present invention (second aspect of the invention)

In the fourth embodiment, the free end portions of the opposing side piece portions 131b, 131b of the absorbent sheet 131 is not extended proximate to the side edges of the back layer 120, and as shown in FIG. 16, the absorbent sheet 131 may be folded again in the neighborhood of the side edges of the back layer 120 and overlaid, so that the same effect as the auiliary sheet can be achieved.

In the fourth embodiment, the absorbent sheet 131 may be folded a larger number of times at the barrier cuff 140, so that a larger number of layers can be formed.

In the fourth embodiment, the multilayer structure at the barrier cuff 140 may be formed by a plurality of absorbent sheets.

In the fourth embodiment, the liquid shrinkable members 150, 150 may be secured to the side of the top layer 110 of the absorbent sheet 131.

In the fourth embodiment, instead of being secured to the absorbent sheet 131, the liquid shrinkable members 150, 150 may be disposed merely between the folding portions of the absorbent sheets 131 and secured thereto only at the longitudinal opposing end portions of the sanitary napkin 101.

In the fourth embodiment, the absorbent sheet 131 and the top layer 110 may be composed of a single sheet.

Figure 17:
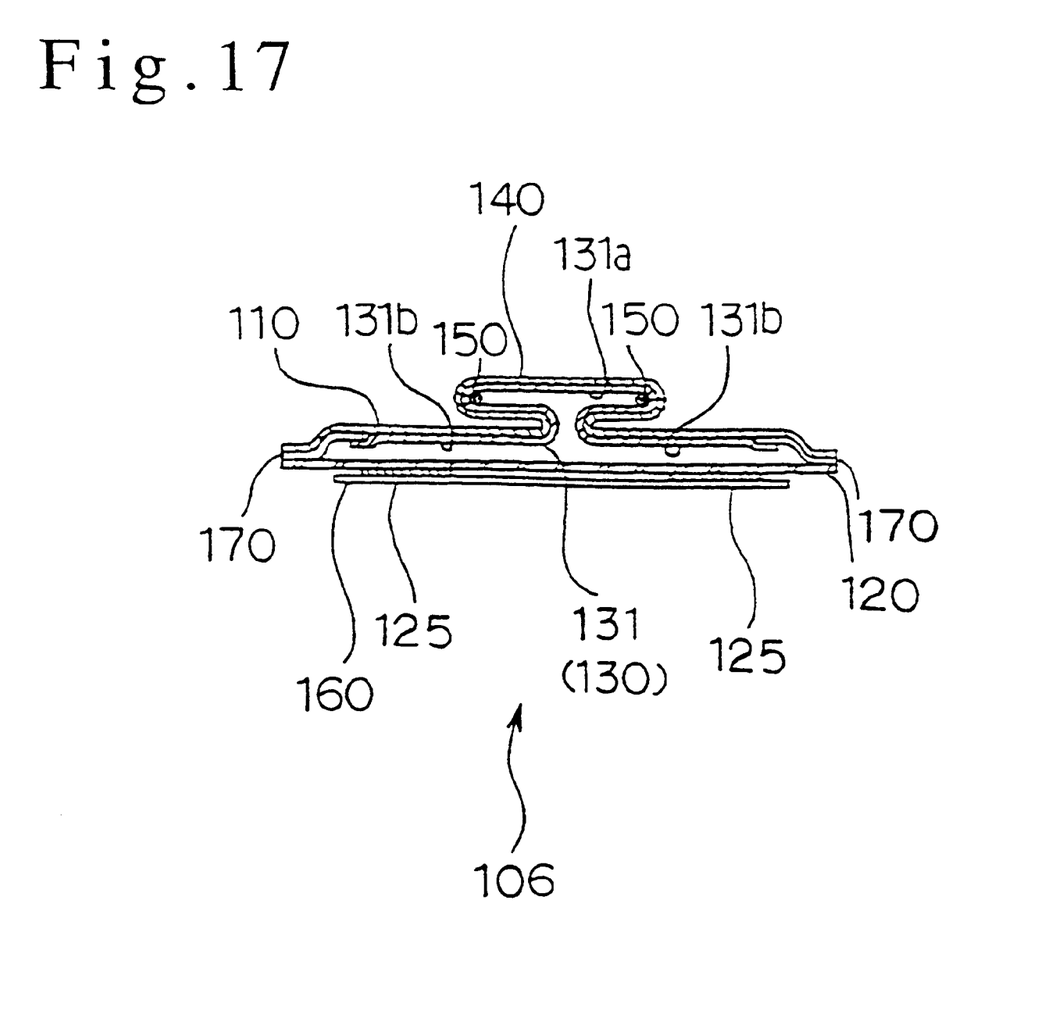
FIG. 17 is a vertical, sectional view corresponding to FIG. 10, showing an absorbent article according to the other embodiment of the present invention (second aspect of the invention).

In the fourth embodiment, it is also acceptable that the side edge portions of the back layer 120 are extended to form leakage preventive walls 120', 120' at the side outwardly of the absorbent member 130 as indicated by dotted lines of FIG. 10, or leakage preventive materials 170, 170 having liquid impermeable properties can be arranged as shown in FIG. 17, so that a possible leakage of body fluid is more reliably prevented. The leakage preventive barriers 120', 120' or the leakage preventive materials 170, 170 may be disposed between the absorbent member 130 and the top layer 110, or they may be arranged outwardly of the top layer 110. In case the leakage preventive barriers 120', 120' and the leakage preventive materials 170, 170 are utilized, the leakage preventive walls 120', 120' or leakage preventive materials 170, 170 are slightly extended in the upward direction by firmly thermally bonding the top layer 110 and the leakage preventive walls 120', 120' or leakage preventive materials 170, 170 to the back layer 120 by heat fusion bonding at the perimeter of the absorbent sheet 131. Due to this arrangement, a more favorable effect can be obtained.

In the fourth embodiment, the absorbent article may be a sanitary napkin, an incontinent pad, a breastfeeding pad, and the like.

INDUSTRIAL APPLICABILITY

As described hereinbefore, according to the absorbent article of the present invention (first aspect of the invention), there can be obtained a favorable body fluid absorptive capacity and a comfortable fitness to the wearer, and the possible leakage of body fluid can be reliably prevented.

As described hereinbefore, according to the absorbent article of the present invention (second aspect of the invention), the absorbent article is effectively bent in the longitudinal direction complying the wearer's contacting part, and nicely fits the wearer so that the possible leakage of body fluid can be effectively prevented, irrespective of the movement of the wearer. Moreover, an absorbent article can easily be manufactured in the state where the liquid shrinkable members do not have elasticity and the absorbent member does not shrink.

What is claimed is:

1. An absorbent article comprising a liquid permeable top layer, a liquid impermeable back layer, and a liquid retentive absorbent member interposed between said top layer and said back layer, wherein said absorbent member includes an absorbent sheet having a thickness of 0.3 mm to 5 mm, and said absorbent sheet is arranged to form an absorbent barrier cuff which is disposed at the central portion of said top layer in the widthwise direction thereof, the entire surface of said absorbent sheet is overlaid with said top layer and said absorbent sheet and said top layer are folded integrally into an overlaying serpentine configuration at folding portions extending in the transverse direction of said absorbent article so that fold lines are created in the longitudinal direction of said absorbent article, thereby providing said barrier cuff, and said barrier cuff has a height of 1 to 30 mm, and is provided with elastic members inside each side edge of said barrier cuff and extending in the longitudinal direction of said barrier cuff such that said barrier cuff shrinks in the longitudinal direction over a prescribed length.

2. The absorbent article according to claim 1, wherein the barrier cuff is 1 mm to 10 mm in height.

3. The absorbent article according to claim 1, wherein said absorbent sheet comprises a central band-like portion and lateral edge portions;

said lateral edge portions being folded inwardly toward each other and further folded outwardly away from each other.

4. The absorbent article according to claim 1, wherein said absorbent sheet contains a superabsorbent polymer.

5. The absorbent article according to claim 4, wherein said superabsorbent polymer is interposed between paper or nonwoven fabrics.

6. The absorbent article according to claim 4, wherein said absorbent sheet is obtainable by admixing a hydrophilic fiber, said superabsorbent polymer and a binder, and forming the admixture into a sheet-like shape.

7. The absorbent article according to claim 6, wherein said absorbent sheet comprises a hydrophilic fiber, a thermally fusible bonding fiber or a strengthening assistant, and said superabsorbent polymer;

said superabsorbent polymer is not present on an absorbent surface of said absorbent sheet for absorbing liquid but distributed inside said absorbent sheet, and is adhered to said hydrophilic fiber constituting said absorbent sheet;

said superabsorbent polymer is spread at an amount of 5 to 300 $gm^2$ of said absorbent sheet; and said absorbent sheet has a thickness of 0.3 to 1.5 mm.

8. A sanitary napkin made of the absorbent article of claim 1.

9. The absorbent article of claim 1, wherein said absorbent member is provided with liquid shrinkable members, which can elastically shrink upon the absorption of a liquid at the surface of said absorbent member facing said top layer and/or inside said absorbent member and in the vicinity of said surface, such that said absorbent member elastically shrinks over a prescribed length, and said absorbent member is arranged to form an absorbent barrier cuff which is disposed at the central portion of said top layer in the widthwise direction thereof, and said liquid shrinkable member is arranged at said barrier cuff.

10. The absorbent article according to claim 1, wherein said liquid shrinkable members are secured to said absorbent sheet, or disposed in the folded portion of said absorbent sheet and secured at longitudinal opposing end portions of said absorbent article.

* * * * *